(12) United States Patent
Garabedian et al.

(10) Patent No.: US 10,524,855 B2
(45) Date of Patent: *Jan. 7, 2020

(54) RADIO FREQUENCY ABLATION COOLING SHIELD

(71) Applicant: Boston Scientific Scimed, Inc., Maple Grove, MN (US)

(72) Inventors: Robert J. Garabedian, Tyngsboro, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 342 days.

This patent is subject to a terminal disclaimer.

(21) Appl. No.: 15/351,993

(22) Filed: Nov. 15, 2016

(65) Prior Publication Data

US 2017/0181791 A1 Jun. 29, 2017

Related U.S. Application Data

(60) Continuation of application No. 14/143,782, filed on Dec. 30, 2013, now Pat. No. 9,526,561, which is a
(Continued)

(51) Int. Cl.
*A61B 18/14* (2006.01)
*A61B 90/00* (2016.01)
*A61B 18/00* (2006.01)

(52) U.S. Cl.
CPC .......... *A61B 18/1477* (2013.01); *A61B 18/14* (2013.01); *A61B 90/04* (2016.02);
(Continued)

(58) Field of Classification Search
CPC ................ A61B 18/14; A61B 18/1477; A61B 2018/00005; A61B 2018/00017;
(Continued)

(56) References Cited

U.S. PATENT DOCUMENTS 4,685,447 A 8/1987 Eastman et al.
5,279,569 A 1/1994 Neer et al.
(Continued)

FOREIGN PATENT DOCUMENTS

WO 9629946 10/1996
WO 0207625 1/2002
(Continued)

OTHER PUBLICATIONS

"Communication Pursuant to Article 94(3) EPC," for European Patent Application No. 04760509.2 dated May 12, 2008 (4 pages).
(Continued)

*Primary Examiner* — Michael F Peffley
(74) *Attorney, Agent, or Firm* — Pauly, DeVries Smith & Deffner LLC

(57) ABSTRACT

A medical assembly and method are provided to effectively treat abnormal tissue, such as, a tumor. The target tissue is thermally ablate using a suitable source, such as RF or laser energy. A cooling shield is placed in contact with non-target tissue adjacent the target tissue, and actively cooled to conduct thermal energy away from the non-target tissue. In one method, the cooling shield can be placed between two organs, in which case, one of the two organs can comprise the target tissue, and the other of the two organs can comprise the non-target tissue. In this case, the cooling shield may comprise an actively cooled inflatable balloon, which can be disposed between the two organs when deflated, and then inflated. The inflated balloon can be actively cooled by pumping a cooling medium through it. In another method, the cooling shield can be embedded within the non-target tissue. In this case, the cooling shield can comprise one or more needles. If a plurality of needles is used, they can be embedded into the non-target tissue in a series, e.g., a rectilinear or curvilinear arrangement. The
(Continued)

needle(s) can be actively cooled by jumping a cooling medium through them.

17 Claims, 13 Drawing Sheets

Related U.S. Application Data continuation of application No. 12/849,699, filed on Aug. 3, 2010, now Pat. No. 8,617,158, which is a division of application No. 11/462,961, filed on Aug. 7, 2006, now abandoned, and a continuation of application No. 10/426,360, filed on Apr. 30, 2003, now Pat. No. 7,101,387.

(52) U.S. Cl.
CPC ........... *A61B 2018/00005* (2013.01); *A61B 2018/00017* (2013.01); *A61B 2018/00023* (2013.01); *A61B 2018/00029* (2013.01); *A61B 2018/00577* (2013.01); *A61B 2090/0445* (2016.02); *A61B 2090/0481* (2016.02)

(58) Field of Classification Search
CPC .......... A61B 2018/00023; A61B 2018/00029; A61B 2018/00577; A61B 90/04; A61B 2090/0445; A61B 2090/0481
See application file for complete search history.

(56) References Cited

U.S. PATENT DOCUMENTS

| | | | |
|---|---|---|---|
| 5,304,214 A * | 4/1994 | DeFord | A61B 18/082 604/916 |
| 5,370,134 A * | 12/1994 | Chin | A61B 17/00234 128/898 |
| 5,415,654 A | 5/1995 | Daikuzono | |
| 5,520,684 A | 5/1996 | Imran | |
| 5,558,672 A | 9/1996 | Edwards et al. | |
| 5,649,973 A * | 7/1997 | Tierney | A61B 18/18 607/101 |
| 5,662,608 A | 9/1997 | Imran et al. | |
| 5,728,143 A | 3/1998 | Gough et al. | |
| 5,735,847 A | 4/1998 | Gough et al. | |
| 5,810,804 A | 9/1998 | Gough et al. | |
| 5,938,659 A | 8/1999 | Tu et al. | |
| 6,015,421 A | 1/2000 | Tanaka et al. | |
| 6,059,780 A | 5/2000 | Gough et al. | |
| 6,090,105 A | 7/2000 | Zepeda et al. | |
| 6,231,570 B1 | 5/2001 | Hata et al. | |
| 6,254,598 B1 | 7/2001 | Utley et al. | |
| 6,379,353 B1 | 4/2002 | Nichols et al. | |
| 6,470,219 B1 | 10/2002 | Edwards et al. | |
| 6,471,695 B1 * | 10/2002 | Behl | A61B 18/16 128/850 |
| 6,494,902 B2 | 12/2002 | Hoey et al. | |
| RE38,143 E | 6/2003 | Dimonda et al. | |
| 6,622,731 B2 | 9/2003 | Russell et al. | |
| 6,743,200 B2 | 6/2004 | Larnard et al. | |
| 6,881,213 B2 | 4/2005 | Ryan et al. | |
| 6,918,907 B2 | 7/2005 | Kelly et al. | |
| 7,101,387 B2 | 9/2006 | Garabedian et al. | |
| 7,749,157 B2 * | 7/2010 | Bertolero | A61B 1/12 600/114 |
| 8,617,158 B2 | 12/2013 | Rioux et al. | |
| 9,526,561 B2 | 12/2016 | Garabedian et al. | |
| 2002/0045893 A1 | 4/2002 | Lane et al. | |
| 2003/0181896 A1 | 9/2003 | Zvuloni et al. | |
| 2004/0220562 A1 | 11/2004 | Garabedian et al. | |
| 2006/0271036 A1 | 11/2006 | Garabedian et al. | |
| 2011/0022044 A1 | 1/2011 | Garabedian et al. | |
| 2014/0324042 A1 | 10/2014 | Garabedian et al. | |

FOREIGN PATENT DOCUMENTS

| | | |
|---|---|---|
| WO | 02089686 | 11/2002 |
| WO | 2004098427 | 11/2004 |

OTHER PUBLICATIONS

"File History," for U.S. Appl. No. 10/426,360, (218 pages).
"File History," for U.S. Appl. No. 11/462,961 (118 pages).
"File History," for U.S. Appl. No. 12/849,699 (231 pages).
"File History," for U.S. Appl. No. 14/143,782 (457 pages).
Goldberg, et al., "Radiofrequency Tissue Ablation: Increased Lesion Diameter with a Perfusion Electrode," Acad Radio!, Aug. 1996, pp. 636-644 (9 pages).
"International Preliminary Report on Patentability," for PCT Application No. PCT/US2004/009685 dated Nov. 4, 2005 (6 pages).
"International Search Report and Written Opinion," for PCT Application No. PCT/US2004/009685 dated Jul. 27, 2004 (9 pages).

* cited by examiner

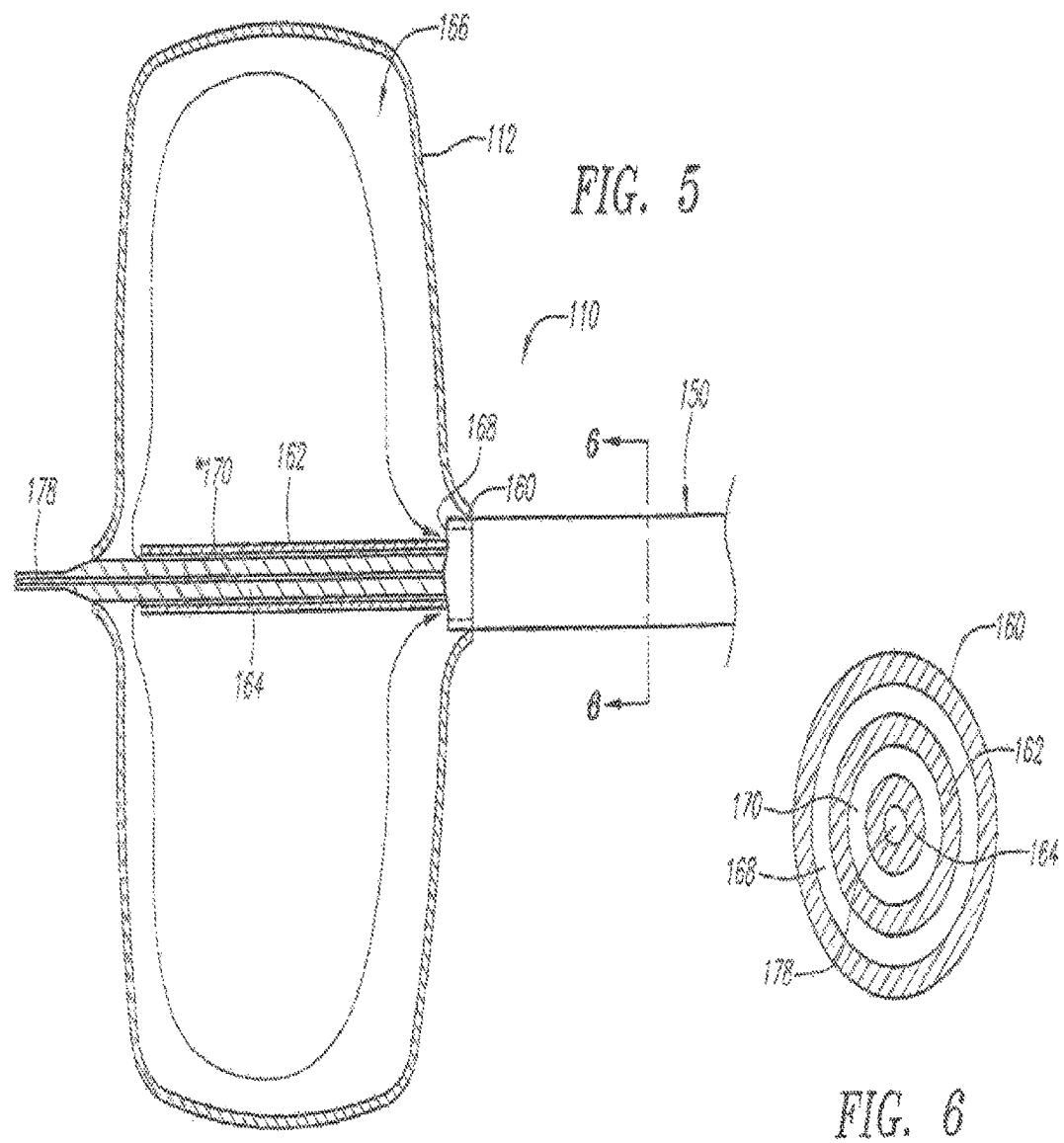

RADIO FREQUENCY ABLATION COOLING SHIELD

CROSS-REFERENCE TO RELATED APPLICATIONS

This application is a continuation of U.S. application Ser. No. 14/143,782, filed on Dec. 30, 2013, now U.S. Pat. No. 9,526,561, which is a continuation of U.S. application Ser. No. 12/849,699, filed on Aug. 3, 2010, now U.S. Pat. No. 8,617,158, which is a division of U.S. application Ser. No. 11/462,961, filed on Aug. 7, 2006, now abandoned, which is a continuation of U.S. application Ser. No. 10/426,360, filed on Apr. 30, 2003, now U.S. Pat. No. 7,101,387.

FIELD OF THE INVENTION

The field of the invention generally relates to the structure and use of ablation to treat tissue abnormalities in a patient, and more particularly, to the use of radio frequency (RF) electrosurgical probes for the treatment of such tissue.

BACKGROUND OF THE INVENTION

The delivery of radio frequency (RF) energy to target regions within tissue is known for a variety of purposes of particular interest to the present inventions. In one particular application, RF energy may be delivered to diseased regions (e.g., tumors) in tissue for the purpose of tissue necrosis. RF ablation of tumors is currently performed within one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. PCT Publication WO 96/29946 and U.S. Pat. No. 6,379,353 disclose such probes.

Whichever technique is used for treatment; the target site, e.g., the tumor, is often dangerously close to vital organs or tissue (e.g., colon, prostate, gall bladder, or diaphragm). In many cases, to prevent or reduce the risk of thermally injuring the vital organs or tissue, the physician will opt to discontinue the procedure, or prematurely stop the procedure, resulting in a high likelihood of re-occurrence.

Thus, there is a need for an improved system and method for protecting vital organs or tissue from thermal damage that may otherwise result during ablation of adjacent tissue.

SUMMARY OF THE INVENTION

In accordance with a first aspect of the present inventions, a medical assembly for cooling tissue is provided. The medical assembly comprises an elongate member and an inflatable cooling balloon mounted to the elongate member. The cooling balloon has an interior region and opposing planar surfaces when inflated. The planar surfaces can be of any shape, e.g., rectangular or oval. The planar surfaces can be curved or straight. The cooling balloon can be compliant, semi-compliant, or non-compliant. In the preferred embodiment, the balloon is configured to be placed between two distinct tissue layers, e.g., two organs. Depending upon the method of delivery, the elongate member can be rigid to facilitate, e.g., an open surgical or percutaneous introduction, or flexible to facilitate, e.g., a laparoscopic introduction. In one embodiment, the elongate member comprises a guide wire lumen, so that the cooling balloon can be guided between the two layers of tissue.

The medical assembly further comprises cooling and return lumens that extend through the elongate member in fluid communication with the interior region of the cooling balloon. In the preferred embodiment, the cooling and return lumens are annular, but can have other configurations. The medical assembly may comprise a cooling pump assembly configured for pumping cooling medium (such as liquid or gas) through the cooling lumen into the interior region of the cooling balloon, and for pumping heated cooling medium from the interior region of the cooling balloon through the return lumen.

Although the present inventions should not be so limited in its broadest aspects, the inflated balloon can be placed between ablation targeted tissue and non-target tissue in order to thermally protect the non-target tissue during ablative treatment of the target tissue.

In accordance with a second aspect of the present inventions, another medical assembly for cooling tissue is provided. The medical assembly comprises an elongated member and an array of actively cooled needles extending from the distal end of the elongate member. The elongate member can be rigid or flexible. The needle array is arranged in a series. By way of non-limiting example, the array of needles can be arranged in a rectilinear or a curvilinear pattern, and can be staggered, fan-shaped, or rake-shaped.

In the preferred embodiment, the needles are configured to be cooled by a liquid medium, such as liquid or gas. In this case, the medical assembly may comprise a cooling pump assembly configured for pumping cooling medium through the needles, and for pumping heated cooling medium from the needles. In one embodiment, the medical assembly comprises a cannula, wherein the elongate member is slidably disposed within the cannula, such that the array of needles can be selectively deployed from the cannula and retracted within the cannula. The cannula can be configured to be introduced percutaneously or laparoscopically into the body of a patient.

Although the present inventions should not be so limited in its broadest aspects, the needle array can be embedded within the tissue along a border between tissue targeted to be ablated and non-target tissue in order to thermally protect the non-target tissue during ablative treatment of the target tissue.

In accordance with a third aspect of the present inventions, a method of performing an ablation procedure is provided. The method comprises thermally ablating target tissue, e.g., a tumor, of a patient. The ablation can be performed using any suitable source of energy, such as, e.g., RF or laser energy. The method further comprises placing a cooling shield in contact with non-target tissue adjacent the target tissue, and actively cooling the cooling shield to conduct thermal energy away from the non-target tissue. If the non-target tissue is within the body of the patient, the cooling shield can be variously introduced therein using a suitable technique, such as, e.g., percutaneously, laparoscopically, or via a surgical opening By way of non-limiting example, the cooling shield can be placed between two organs, in which case, one of the two organs can comprise the target tissue, and the other of the two organs can comprise the non-target tissue. In this case, the cooling shield may comprise an actively cooled inflatable balloon, which can be disposed between the two organs when deflated, and then inflated. The inflatable balloon can be guided between the two organs using a guide wire. The inflatable balloon can be actively cooled by pumping a cooling medium through it.

By way of further non-limiting example, the cooling shield can be embedded within the non-target tissue. In this case, the cooling shield can comprise one or more needles. If a plurality of needles is used, they can be embedded into the non-target tissue in a series, e.g., a rectilinear or curvilinear arrangement. The needle(s) can be actively cooled by pumping a cooling medium through them.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 5 is a partially cut-away cross-sectional view of the cooling probe of FIG. 4;

FIG. 6 is a cross-sectional view of the cooling probe of FIG. 5 taken along the line 6-6;

DETAILED DESCRIPTION OF THE PREFERRED EMBODIMENTS

Figure 1:
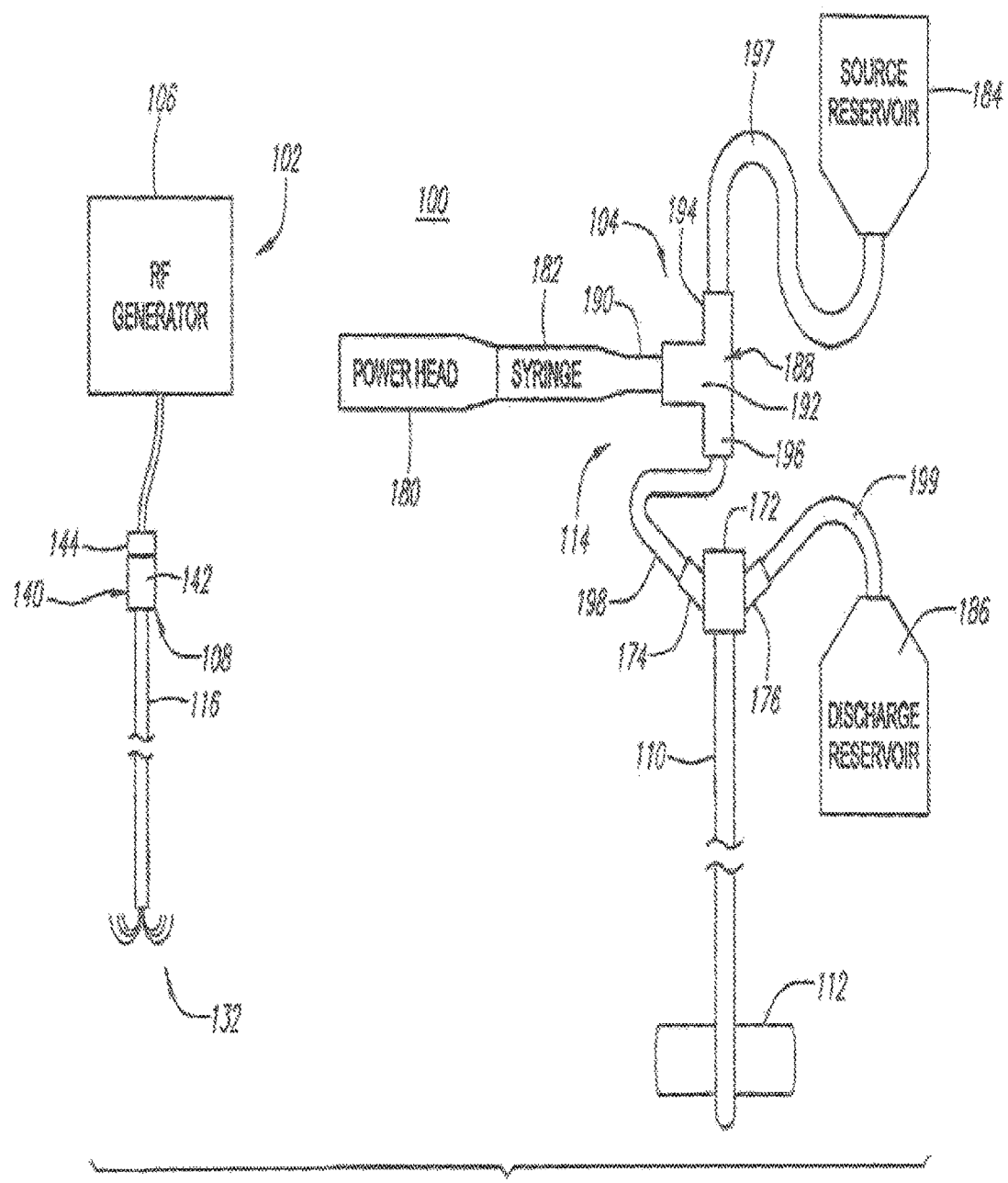
FIG. 1 is a plan view of a tissue treatment system constructed in accordance with one preferred embodiment of the present inventions.

FIG. 1 illustrates a tissue treatment system 100 constructed in accordance with a preferred embodiment of the present inventions. The tissue treatment system 100 comprises a tissue ablation subsystem 102, which generally includes an ablation probe assembly 106 configured for introduction into the body of a patient for ablative treatment of target tissue (e.g., a tumor), and a radio frequency (RF) generator 108 configured for supplying RF energy to the ablation probe assembly 106 in a controlled manner. The tissue treatment system 100 further comprises a tissue cooling subsystem 104, which generally includes a cooling probe 110 with an associated active cooling shield 112 configured for being effectively placed in contact with non-target tissue (e.g., a vital organ adjacent the tumor), and an active cooling unit 114 configured for actively removing thermal energy away from the cooling shield 112, and thus, the non-target tissue, during the ablation procedure.

Figure 2:
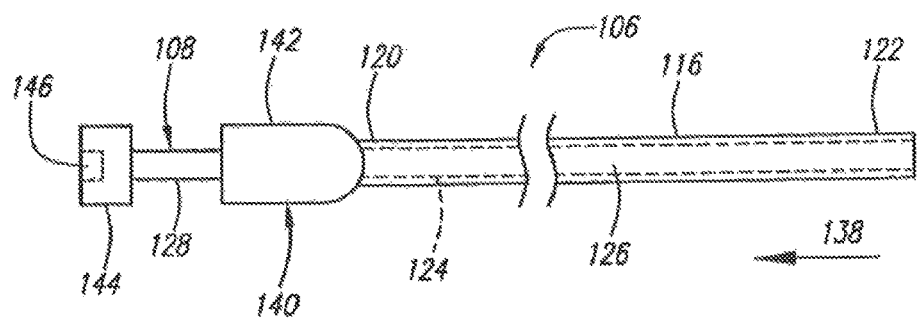
FIG. 2 is a side view of an ablation probe assembly used in the tissue treatment system of FIG. 1, wherein a needle electrode array is particularly shown retracted.
Figure 3:
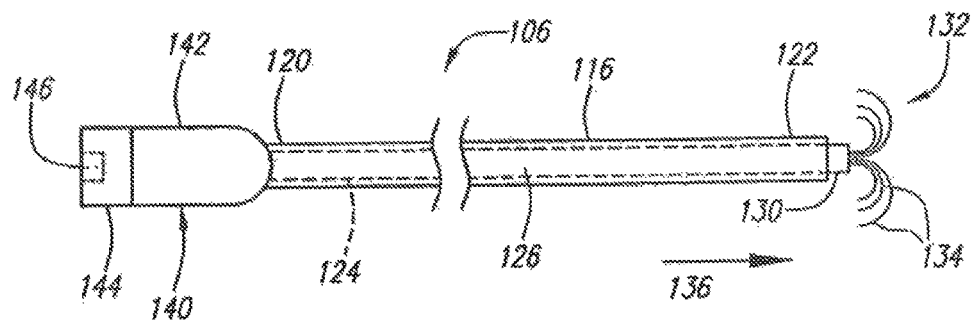
FIG. 3 is a side view of an ablation probe assembly used in the tissue treatment system of FIG. 1, wherein the needle electrode array is particularly shown deployed.

Referring specifically to FIGS. 2 and 3, the ablation probe assembly 106 generally comprises an elongate cannula 116 and an inner probe 118 slidably disposed within the cannula 116. As will be described in further detail below, the cannula 116 serve to deliver the active portion of the inner probe 118 to the target tissue. The cannula 116 has a proximal end 120, a distal end 122, and a central lumen 124 (shown in phantom) extending between the proximal and distal ends 120 and 122. As will be described in further detail below, the cannula 116 may be rigid, semi-rigid, or flexible depending upon the designed means for introducing the cannula 116 to the target tissue. The cannula 116 is composed of a suitable material, such as plastic, metal, or the like, and has a suitable length, typically in the range from 5 cm to 30 cm, preferably from 10 cm to 20 cm. If composed of an electrically conductive material, the cannula 108 is preferably covered with an insulative material. The cannula 116 has an outside diameter consistent with its intended use, typically being from 1 mm to 5 mm, usually from 1.3 mm to 4 mm. The cannula 116 has an inner diameter in the range from 0.7 mm to 4 mm, preferably from 1 mm to 3.5 mm.

The inner probe 118 comprises a reciprocating shaft 126 having a proximal end 128 and a distal end 130, and an array 132 of tissue penetrating needle electrodes 134 extending from the distal end 130 of the shaft 126. Like the cannula 116, the shaft 126 is composed of a suitable material, such as plastic, metal or the like. It can be appreciated that longitudinal translation of the shaft 126 relative to the cannula 116 in a distal direction 136 deploys the electrode array 132 from the distal end 122 of the cannula 116 (FIG.

3), and longitudinal translation of the shaft 126 relative to the cannula 116 in a proximal direction 138 retracts the electrode array 132 into the distal end 122 of the cannula 116 (FIG. 2).

Each of the individual needle electrodes 134 is in the form of a small diameter metal element, which can penetrate into tissue as it is advanced from a target site within the target region. When retracted within the cannula 116 (FIG. 2), the electrode array 132 is placed in a radially collapsed configuration, and the individual needle electrodes 134 are constrained and held in generally axially aligned positions within the cannula 116 to facilitate its introduction to the tissue target site. The ablation probe assembly 106 optionally includes a core member (not shown) mounted to the distal tip of the shaft 126 and disposed within the center of the electrode array 132. In this manner, substantially equal circumferential spacing between the needle electrodes 134 is maintained when retracted within the central lumen 124 of the cannula 116.

When deployed from the cannula 116 (FIG. 3), the electrode array 132 is placed in a three-dimensional configuration that usually defines a generally ellipsoidal or spherical volume having a periphery with a maximum radius in the range from 0.5 cm to 3 cm. The needle electrodes 134 are resilient and pre-shaped to assume a desired configuration when advanced into tissue. In the illustrated embodiment, the needle electrodes 134 diverge radially outwardly from the cannula 116 in a uniform pattern, i.e., with the spacing between adjacent needle electrodes 134 diverging in a substantially uniform and/or symmetric pattern. In the illustrated embodiment, the needle electrodes 134 also evert proximally, so that they face partially or fully in the proximal direction 138 when fully deployed. In exemplary embodiments, pairs of adjacent needle electrodes 134 can be spaced from each other in similar or identical, repeated patterns that can be symmetrically positioned about an axis of the shaft 126. It will be appreciated that a wide variety of particular patterns can be provided to uniformly cover the region to be treated. It should be noted that a total of six needle electrodes 134 are illustrated in FIG. 3. Additional needle electrodes 134 can be added in the spaces between the illustrated electrodes 134, with the maximum number of needle electrodes 134 determined by the electrode width and total circumferential distance available (i.e., the needle electrodes 134 could be tightly packed).

Each individual electrode 134 is preferably composed of a single wire that is formed from resilient conductive metals having a suitable shape memory, such as stainless steel, nickel-titanium alloys, nickel-chromium alloys, spring steel alloys, and the like. The wires may have circular or non-circular cross-sections, but preferably have rectilinear cross-sections. In this manner, the needle electrodes 134 are generally stiffer in the transverse direction and more flexible in the radial direction. By increasing transverse stiffness, proper circumferential alignment of the needle electrodes 134 within the cannula 116 is enhanced. Exemplary needle electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm.

The distal ends of the needle electrodes 134 may be honed or sharpened to facilitate their ability to penetrate tissue. The distal ends of these needle electrodes 134 may be hardened using conventional heat treatment or other metallurgical processes. They may be partially covered with insulation, although they will be at least partially free from insulation over their distal portions. The proximal ends of the needle electrodes 134 may be directly coupled to the connector assembly (described below), or alternatively, may be indirectly coupled thereto via other intermediate conductors, e.g., RF wires. Optionally, the shaft 126 and any component between the shaft 126 and the needle electrodes 134, are composed of an electrically conductive material, such as stainless steel, and may therefore conveniently serve as intermediate electrical conductors.

In the illustrated embodiment, the RF current is delivered to the electrode array 132 in a monopolar fashion, which means that current will pass from the electrode array 132, which is configured to concentrate the energy flux in order to have an injurious effect on the surrounding tissue, and a dispersive electrode (not shown), which is located remotely from the electrode array 132 and has a sufficiently large area (typically 130 cm$^2$ for an adult), so that the current density is low and non-injurious to surrounding tissue. As previously described, however, inadvertent damage to surrounding tissue cannot always be avoided. In the illustrated embodiment, the dispersive electrode may be attached externally to the patient, e.g., using a contact pad placed on the patient's flank. In a monopolar arrangement, the needle electrodes 134 are bundled together with their proximal portions having only a single layer of insulation over the cannula 116.

Alternatively, the RF current is delivered to the electrode array 132 in a bipolar fashion, which means that current will pass between "positive" and "negative" electrodes 134 within the array. In a bipolar arrangement, the positive and negative needle electrodes 134 will be insulated from each other in any regions where they would or could be in contact with each other during the power delivery phase.

Further details regarding needle electrode array-type probe arrangements are disclosed in U.S. Pat. No. 6,379,353, entitled "Apparatus and Method for Treating Tissue with Multiple Electrodes," which is hereby expressly incorporated herein by reference.

The ablation probe assembly 106 further comprises a handle assembly 140, which includes a connector sleeve 142 mounted to the proximal end 120 of the cannula 116 and a connector member 144 slidably engaged with the sleeve 142 and mounted to the proximal end 128 of the shaft 126. The connector member 144 also comprises an electrical connector 146 (in phantom) in which the proximal ends of the needle electrodes 134 (or alternatively, the intermediate conductors) extending through the shaft 126 of the inner probe 118 are coupled. The handle assembly 140 can be composed of any suitable rigid material, such as, e.g., metal, plastic, or the like.

The ablation probe assembly 106 may optionally have active cooling functionality, in which case, a heat sink (not shown) can be mounted within the distal end 130 of the shaft 126 in thermal communication with the electrode array 132, and cooling and return lumens (not shown) can extend through the shaft in fluid communication with the heat sink to draw thermal energy away back to the proximal end of the shaft 126. A pump assembly (not shown) can be provided to convey a cooling medium through the cooling lumen to the heat sink, and to pump the heated cooling medium away from the heat sink and back through the return lumen. Further details regarding active cooling of the electrode array 132 are disclosed in copending U.S. application Ser. No. 10/426,360.

Referring back to FIG. 1, the RF generator 108 is electrically connected to the electrical connector 146 of the handle assembly 140, which as previously described, is directly or indirectly-electrically coupled to the electrode array 132. The RF generator 108 is a conventional RF power supply that operates at a frequency in the range of 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion.

Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as RadioTherapeutics of Mountain View, Calif., which markets these power supplies under the trademarks RF2000™ (100 W) and RF3000™ (200 W).

Figure 4:
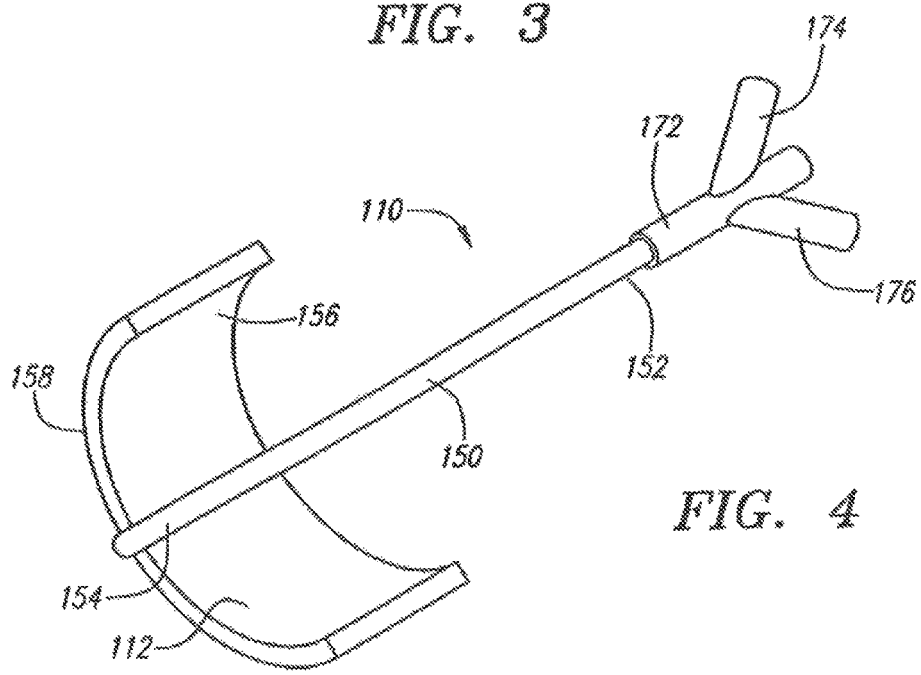
FIG. 4 is a perspective view of a cooling probe used in the tissue treatment system of FIG. 1.

Referring now to FIG. 4, the cooling probe 110 comprises an elongate catheter shaft 150 having a proximal end 152 and a distal end 154. The catheter shaft 150 is composed of a flexible biocompatible material, such as, e.g., polyurethane or polyethylene, and has a suitable diameter, e.g., 7F. In this embodiment, the cooling shield 112 is an inflatable balloon that is mounted to the distal end 154 of the catheter shaft 150. In the illustrated embodiment, the balloon 112 is bonded to the catheter shaft 150 by a suitable adhesive, for example, epoxy adhesives, urethane adhesives, cyanoacrylates, and other adhesives suitable for bonding nylon or the like, as well as by hot melt bonding, ultrasonic welding, heat fusion or the like. Alternatively, the balloon may be integrally molded with the catheter shaft 150 or may be attached to the catheter shaft 150 by mechanical means such as swage locks, crimp fittings, threads, and the like.

As illustrated in FIG. 4, the balloon 112 exhibits a substantially thin profile, when expanded, so that it can be effectively located between adjacent planes of tissue, such as, e.g., two organs. That is, the balloon 112 has a pair of opposing planar surfaces 156 and 158 that are laterally spaced from each other a small distance, so that the expanded balloon 112 can easily fit between and conform to the adjacent planes of tissue. The planar surfaces 156 and 158 of the balloon 112 have a rectangular shape, but can have other shapes (e.g., oval, oblong, triangular, trapezoidal, etc.) depending upon the specific tissue planes between which the balloon 112 is intended to be located. It is noted that, in the illustrated embodiment, the planar surfaces 156 and 158 are curved, so that the balloon 112 will conform to the curved surface of an organ. The balloon 112 can be of any dimension that allows it to be effectively placed between the desired planes of tissue, so that the non-target tissue is protected.

The balloon 112 can be composed of a suitable compliant, semi-compliant, or non-compliant, such as, e.g., polyethylene, nylon, polyamide, polyether block amides (PEBAX), polyethylene terephthalate (PET), silicone, POC, polypropylene, polyether block PBT, and the like. In addition, the balloon 112 may be formed of multiple layers of these materials and/or be coextruded. Further, the balloon 112 may comprise fiber reinforcements. Preferably, the balloon 112 exhibits some non-compliancy so that it can inflate between the adjacent planes of tissue. If non-compliant, the balloon 112 can be manually folded or collapsed onto the distal end 154 of the catheter shaft 150 and held in place using suitable securing means (not shown) to maintain a low profile when introduced into the body of the patient. The securing means can then be released when the balloon 112 is to be inflated. If the balloon 112 exhibits enough compliancy, the balloon 112 will naturally have a low profile when deflated, possibly obviating the need to manually fold or collapse the balloon 112. Depending upon its size, however, the balloon 112, whether compliant or not, may need to be folded and secured to ensure that it exhibits a low profile when not inflated.

Referring now to FIGS. 5 and 6, the catheter shaft 150 comprises an outer tubular element 160, an inner tubular element 162 that resides within, and extends distally from, the outer tubular element 160, and a central tubular element 164 that resides within, and extends distally from, the inner tubular element 162. The cooling probe 110 comprises a coolant flow conduit that is in fluid communication with an interior region 166 of the balloon 112. The coolant flow conduit serves to cool the external surface of the balloon 112, and thus the tissue in contact with the balloon 112, by thermally drawing heat away from the balloon 112. In particular, the coolant flow conduit comprises a cooling lumen 168 that is configured for conveying a suitable cooling medium (such as, e.g., a liquid or gas) into the interior region 166 of the balloon 112, and a return lumen 170 that is configured for conveying the heated cooling medium from the interior region 166 of the balloon 112. Preferably, the cooling medium is composed of saline that is cooled to just above the cryotemperature that would cause unintended necrosis of tissue. It should be noted that for the purposes of this specification, however, a cooled medium is any medium that has a temperature suitable for drawing heat away from the tissue. For example, a cooled medium at room temperature or lower may be suited for cooling tissue during ablation under certain circumstances.

In the illustrated embodiment, the cooling lumen 168 is an annular lumen that is formed between the inner and central tubular elements 162 and 164, and the return lumen 170 is an annular lumen that is formed between the outer and inner tubular elements 160 and 162. Alternatively, the annular lumen formed between the inner and central tubular elements 162 and 164 can be the return lumen 170, and the annular lumen formed between the outer and inner tubular elements 160 and 162 can be the cooling lumen 168. It should be noted that the cooling and return lumens 168 and 170 need not be coaxial, but can be disposed within the catheter shaft 150 in a side-by-side relationship. In any event, the cooling and return lumens 168 and 170 preferably terminate in opposite ends of the interior region 166 of the balloon 112 to provide a more efficient flow of the medium through the interior region 166 of the balloon 112 (as shown by the arrows), i.e., the medium will flow through the entire length of the balloon 112.

Referring back to FIG. 4, the cooling probe 110 further comprises a handle 172 mounted to the proximal end 152 of the catheter shaft 150. The handle 172 is configured to mate with the active cooling unit 114, which as will be discussed below, takes the form of a pump assembly. To this end, the handle 172 comprises an inlet fluid port 174, which is in fluid communication with the cooling lumen 168, and an outlet fluid port 176, which is in fluid communication with the return lumen 170. The handle assembly 140 can be composed of any suitable rigid material, such as, e.g., metal, plastic, or the like.

In the illustrated embodiment, the cooling probe 110 is configured to be laparoscopically introduced into the pertinent body cavity of the patient and guided between the tissue planes with a guide wire. To this end, the cooling probe 110 comprises a guide wire lumen 178 (shown in FIG. 5), which is formed by the central lumen of the central tubular element 164. So that the cooling probe 110 can be tracked over the guide wire, the catheter shaft 150 is preferably composed of a flexible biocompatible material. Alternatively, a semi-rigid sheath can be used to guide the cooling probe 110. Even more alternatively, the cooling probe 110 may be configured to be percutaneously inserted into the pertinent body cavity (e.g., using a direct chest puncture), in which case, a rigid shaft can be used in place of the flexible catheter shaft 150. The rigid shaft can also be reciprocatably disposed within a cannula 116 in a manner similar to that described above with respect to the ablation probe assembly 106. The rigid shaft can even be used to facilitate manual placement of the balloon 112 in an open surgical setting with or without the cannula.

Referring back to FIG. 1, the pump assembly 114 comprises a power head 180 and a syringe 182 that is front-loaded on the power head 180 and is of a suitable size, e.g., 200 ml. The power head 180 and the syringe 182 are conventional and can be of the type described in U.S. Pat. No. 5,279,569 and supplied by Liebel-Flarsheim Company of Cincinnati, Ohio. The pump assembly 114 further comprises a source reservoir 184 for supplying the cooling medium to the syringe 182, and a discharge reservoir 186 for collecting the heated medium from cooling probe 110. The pump assembly 114 further comprises a tube set 188 removably secured to an outlet 190 of the syringe 182. Specifically, a dual check valve 192 is provided with first and second legs 194 and 196, of which the first leg 194 serves as a liquid inlet connected by tubing 197 to the source reservoir 184. The second leg 196 is an outlet leg and is connected by tubing 198 to the inlet fluid port 174 on the connector 170 of the cooling probe 110. The discharge reservoir 186 is connected to the outlet fluid port 176 on the connector 170 of the cooling probe 110 via tubing 199.

Thus, it can be appreciated that the pump assembly 114 can be operated to periodically fill the syringe 182 with the cooling medium from the source reservoir 184, and convey the cooling medium from the syringe 182, through the tubing 198, and into the inlet fluid port 174 on the handle 172. Heated medium is conveyed from the outlet fluid port 176 on the handle 172, through the tubing 198, and into the collection reservoir 186. The pump assembly 114, along with the RF generator 108, can include control circuitry to automate or semi-automate the cooled ablation process.

Having described the structure of the tissue ablation system 100, its operation in treating targeted tissue will now be described. The treatment region may be located anywhere in the body where hypothermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques-capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally. A contrast agent, such as an echogenic fluid, can be used as the cooled medium, so that the balloon 112 of the cooling probe 110 can be visualized using.

Figure 7A:
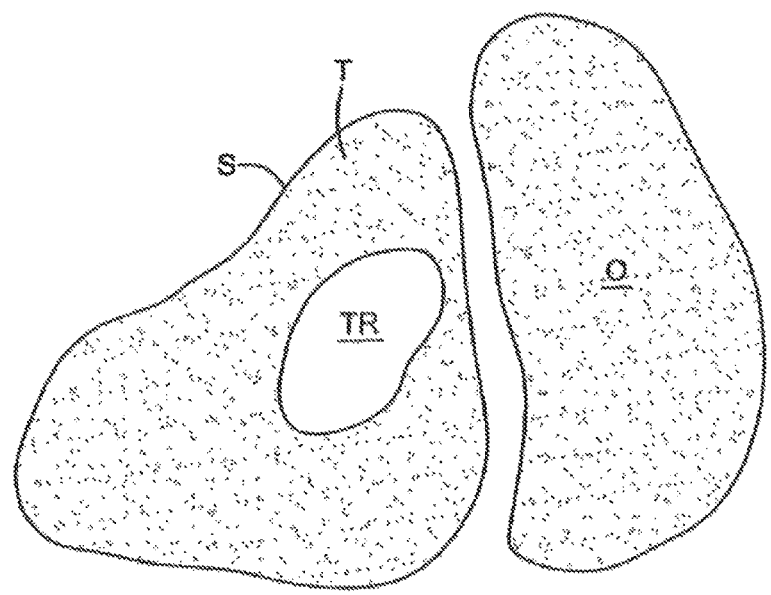
FIGS. 7A-7G-illustrate cross-sectional views of one preferred method of using the tissue treatment system of FIG. 1 to treat target tissue, wherein the cooling probe of FIG. 4 is used to thermally protect adjacent tissue.
Figure 7B:
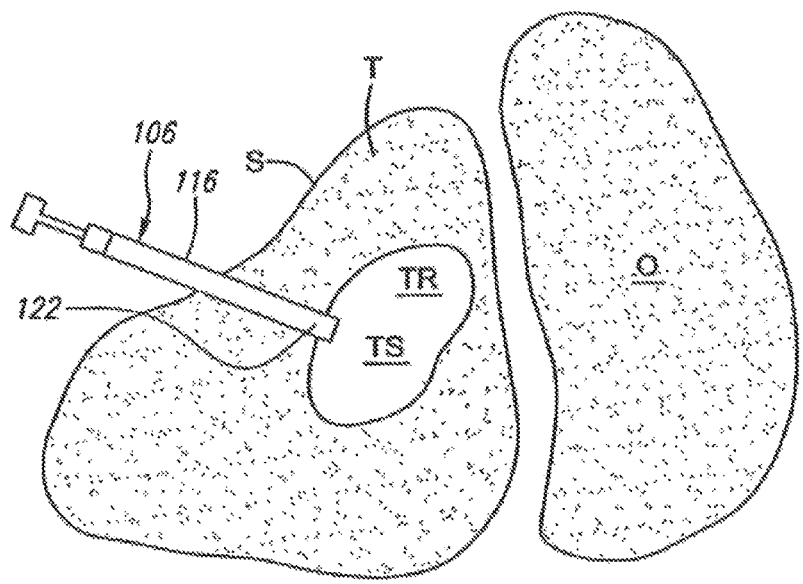

Referring now to FIGS. 7A-7G, the operation of the tissue treatment system 100 is described in treating a treatment region TR within a tissue T located beneath the skin or an organ surface S of a patient. The tissue T, and an adjacent organ O, prior to treatment is shown in FIG. 7A. The ablation probe assembly 106 is introduced within the treatment region TR, so that the distal end 122 of the cannula 116 is located at the target site TS, as illustrated in FIG. 7B. This can be accomplished using any one of a variety of techniques. In some cases, the cannula 116 and inner probe 118 may be introduced to the target site TS percutaneously directly through the patient's skin or through an open surgical incision. In this case, the cannula 116 may have a sharpened tip, e.g., in the form of a needle, to facilitate introduction to the treatment region TR. In such cases, it is desirable that the cannula 116 or needle be sufficiently rigid, i.e., have a sufficient column strength, so that it can be accurately advanced through tissue. In other cases, the cannula 116 may be introduced using an internal stylet that is subsequently exchanged for the shaft 150 and electrode array 132. In this latter case, the cannula 116 can be relatively flexible, since the initial column strength will be provided by the stylet. More alternatively, a component or element may be provided for introducing the cannula 116 to the treatment region TR. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 116 and inner probe 118 can then be introduced through the sheath lumen, so that the distal end 122 of the cannula 116 advances from the sheath into the target site TS.

Figure 7C:
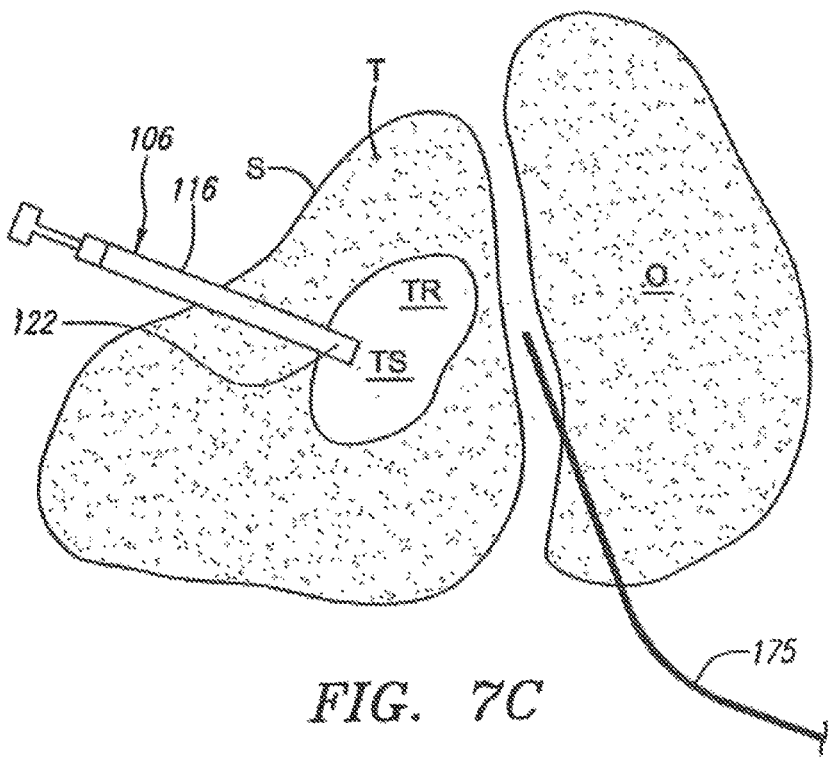
Figure 7D:
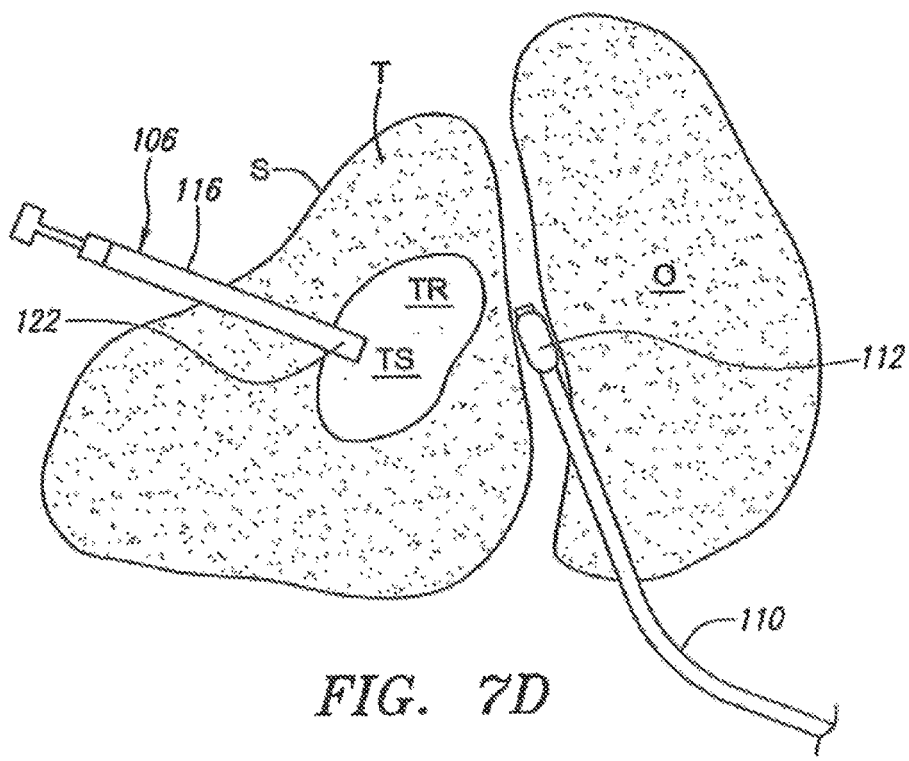

A guide wire 175 is then laparoscopically introduced within the body of the patient and advanced to a location between the treatment region TR and the organ O, as illustrated in FIG. 7C. The cooling probe 110 is then advanced over the guide wire 175 until the uninflated balloon 112 resides between the treatment region TR and the organ O, as illustrated in FIG. 7D. Alternatively, the cooling probe 110 can percutaneously or laparoscopically deliver the balloon 112 between the treatment region TR without the use of the guide wire 175 in the same manner that the ablation probe assembly 106 is delivered to the treatment region TR.

Figure 7E:
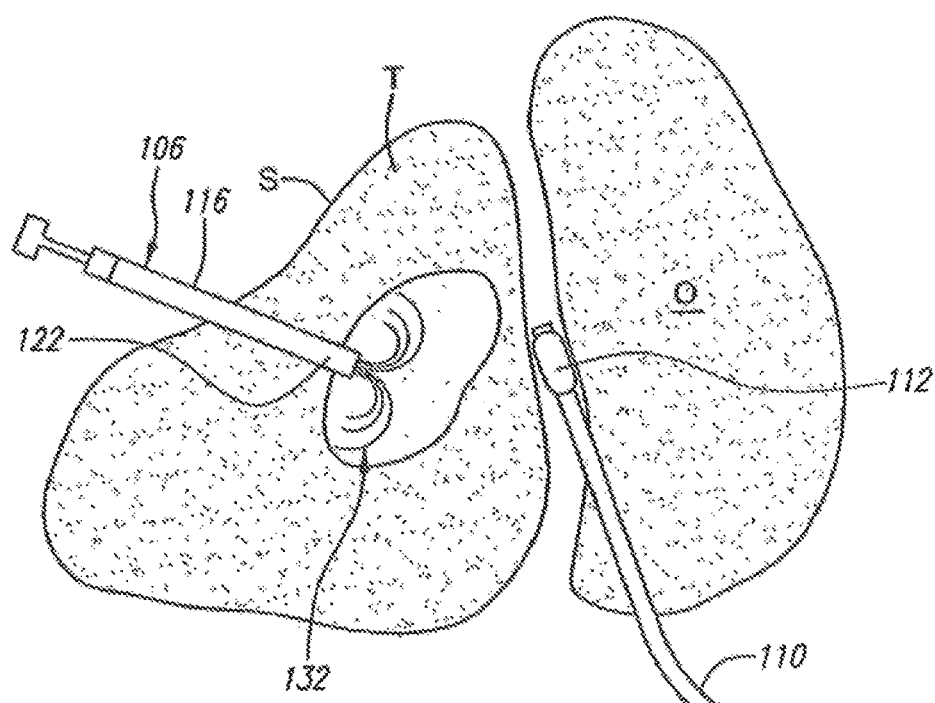

After the cannula 116 and cooling probe 110 are properly placed, the shaft 150 of the ablation probe assembly 106 is distally advanced to deploy the electrode array 132 radially outward from the distal end 122 of the cannula 116 until the electrode array 132 fully everts in order to circumscribe substantially the entire treatment region TR, as illustrated in FIG. 7E.

Figure 7F:
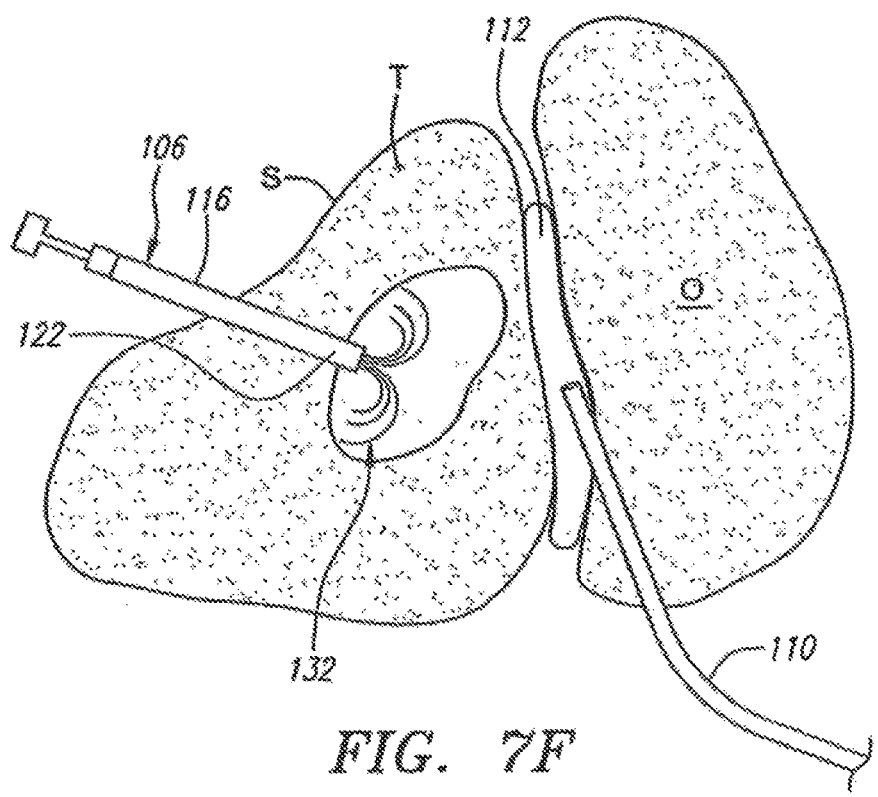

The RF generator 108 is then connected to the electrical connector 146 of the ablation probe assembly 106, and the pump assembly 114 is connected to fluid ports 174 and 176 of the cooling probe 110. The pump assembly 114 is then operated to inflate and convey the cooling medium through the balloon 112, thereby providing a thermal barrier between the treatment region TR and the organ O, as illustrated in FIG. 7F. Specifically, the power head 180 conveys the cooled medium from the syringe 182 under positive pressure, through the tubing 198, and into the inlet fluid port 174 on the handle 172. The cooled medium then travels through the cooling lumen 168 and into the interior region 166 of the balloon 112. Thermal energy is transferred from the treatment region TR, to the balloon 112, and then to the cooled medium, thereby preventing the thermal energy from reaching the organ O at a cool temperature. The heated medium is then conveyed from the interior region of the balloon 112 back through the return lumen 170. From the return lumen 170, the heated medium travels through the outlet fluid port 176 on the handle 172, through the tubing 199, and into the discharge reservoir 186.

Figure 7G:
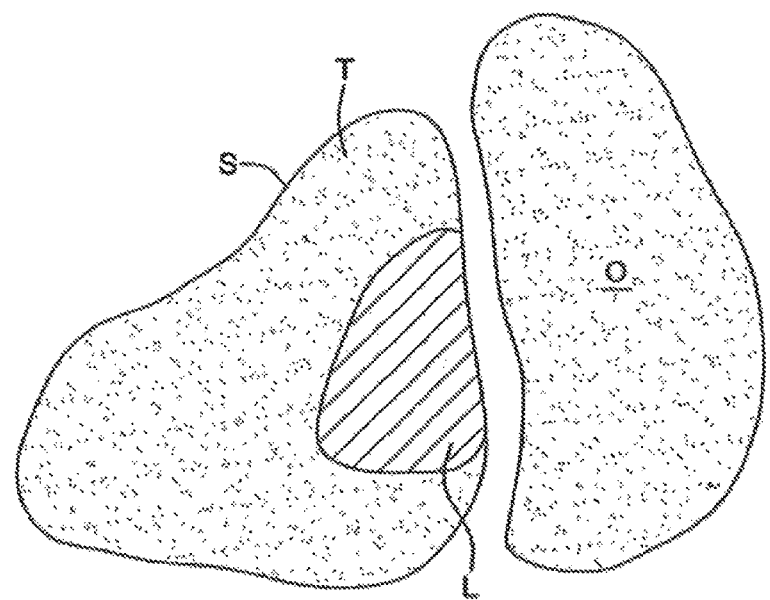

The RF generator 108 is then operated to ablate the treatment region TR. Specifically, a lesion L is formed within the treatment region TR, as illustrated in FIG. 7G. Because the actively cooled balloon 112 forms a thermal barrier between the treatment region TR and the organ O, the lesion L does not extend to the organ O.

Figure 8:
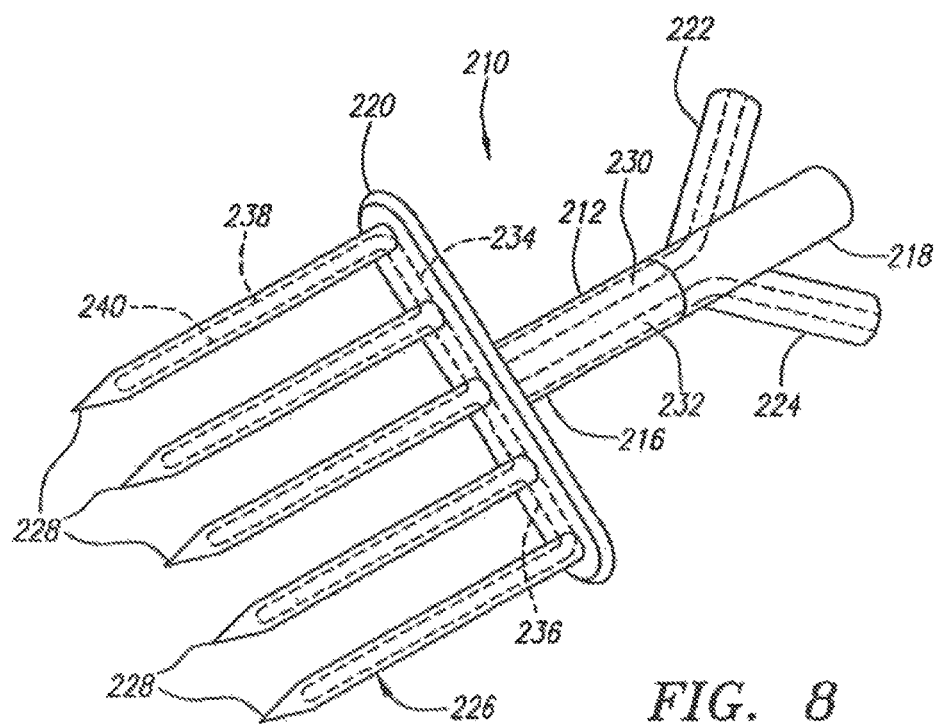
FIG. 8 is a side view of a cooling probe that can be used in the tissue treatment system of FIG. 1, particularly showing a needle array in a rectilinear configuration.

Referring to FIG. 8, another cooling probe 210 that can be used in the cooling subsystem 104 is illustrated. The cooling probe 210 comprises a shaft 212 having a proximal end 214 and a distal end 216. The cooling probe 210 further comprises a handle 218 mounted to the proximal end 214 of the shaft 212, and a cross-member 220 mounted to the distal end 216 of the shaft 212. The cross-member 220 can be integrally formed with the shaft 212 to form a unibody design, or can be suitably bonded, welded, or mechanically attached to the shaft 212. Like the previously described handle assembly 140, the handle 218 comprises an inlet fluid port 222 and an outlet fluid port 224. In this embodiment, the cooling shield 112 comprises an array 226 of tissue penetrating cooling needles 228 that is mounted to the cross-member 220. The needles 228 can be integrally formed with the cross-member to form a unibody design, or can be suitably bonded, welded, or mechanically attached to the cross-member 220. The shaft 212, cross-member 220, and needles 228 are formed of a suitable rigid material, such as, e.g., stainless steel. The diameter and length of the needles 228 are preferably within the range of 0.5 mm to 4.0 mm, and 5 cm to 25 cm, respectively.

Figure 9:
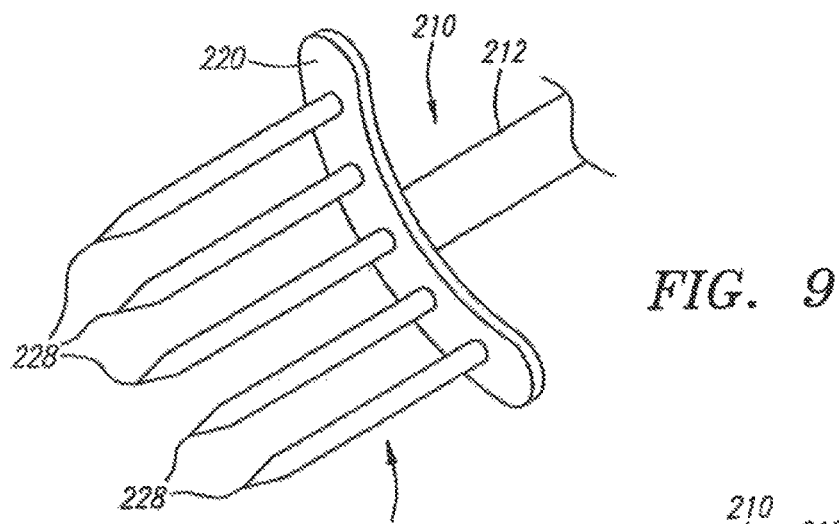
FIG. 9 is a side view of a cooling probe that can be used in the tissue treatment system of FIG. 1, particularly showing a needle array in a curvilinear configuration.
Figure 10:
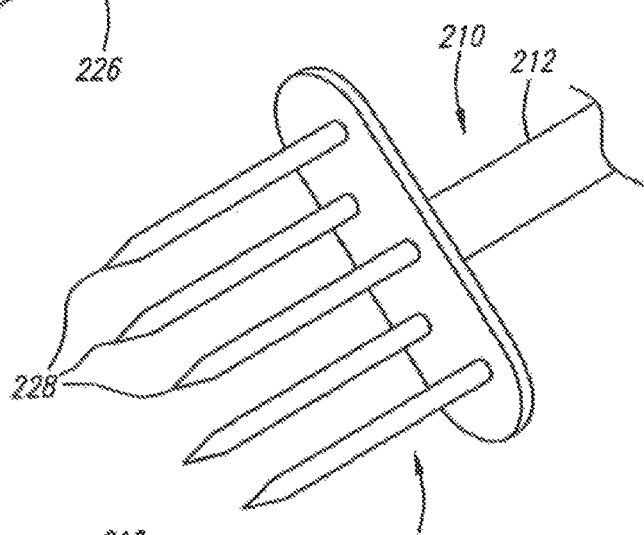
FIG. 10 is a side view of a cooling probe that can be used in the tissue treatment system of FIG. 1, particularly showing a needle array in a staggered configuration.
Figure 11:
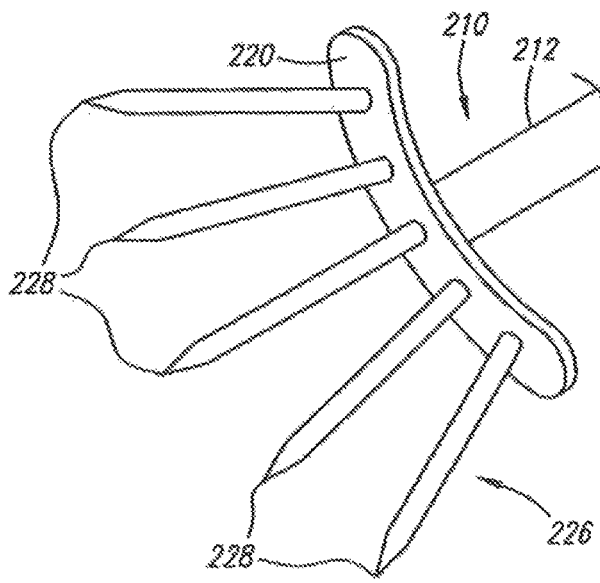
FIG. 11 is a side view of a cooling probe that can be used in the tissue treatment system of FIG. 1, particularly showing a needle array in a rake-shaped configuration.

As illustrated in FIG. 8, the needles 228 are arranged in a series to maximize the cooling efficiency of cooling probe 210, i.e., the span of the needle array 226 is maximized, thereby allowing larger non-target tissue regions to be thermally protected. In the illustrated embodiment, the needle array 226 is arranged in a rectilinear pattern. It should be noted, that depending upon the contour of the non-target tissue, the needle array 226 can also be arranged in a curvilinear pattern, as illustrated in FIG. 9. The needles 228 can also be staggered if additional thermal protection is required, as illustrated in FIG. 10. Although, in the illustrated embodiment, the needles 228 are shown parallel to each other, they can also be non-parallel, e.g., a rake-shape, as illustrated in FIG. 11.

Referring back to FIG. 8, the cooling probe 210 further comprises a coolant flow conduit (shown in phantom) that serves to cool the needles 228, and thus the tissue in contact with the balloon 112, by thermally drawing heat away. In particular, the coolant flow conduit comprises a main cooling lumen 230 that is in fluid communication with the inlet fluid port 222 of the handle 218 and extends through the shaft 212, a common cooling lumen 234 that is in fluid communication with the main cooling lumen 230 and extends through the cross-member 220, and a plurality of branched cooling lumens 238 that is in fluid communication with the common cooling lumen 234 and extends through the needles 228. The coolant flow conduit also comprises a main return lumen 232 that is in fluid communication with the outlet fluid port 224 of the handle 218 and extends through the shaft 212, a common return lumen 236 that is in fluid communication with the main return lumen 232 and extends through the cross-member 220, and a plurality of branched return lumens 240 that is in fluid communication with the common return lumen 236 and extends through the needles 228. The distal ends of the branched cooling lumens 238 are in fluid communication with the respective distal ends of the branched return lumens 240 to complete the cooling circuit.

Operation of the cooling probe 210 is similar to that previously described with the exception that it is designed to be inserted into the tissue during an open surgical setting. Specifically, the electrode array 132 of the ablation probe assembly 106 is deployed within the target tissue TR, as illustrated in FIG. 7. The needle array 226 of the cooling probe 210 is inserted within the tissue, so that the needles 228 lie along a boundary B separating the treatment region TR from the non-treatment region NTR, as illustrated in FIG. A.

The pump assembly 114 is then operated to convey the cooling medium through the needles 228, thereby providing a thermal barrier between the treatment region TR and the non-treatment region NTR. Specifically, the power head 180 conveys the cooled medium from the syringe 182 under positive pressure, through the tubing 198, and into the inlet fluid port 222 on the handle 218. The cooled medium then travels through the main cooling lumen 230, through the common cooling lumen 234, and into the branched cooling lumens 238 within the needles 228. Thermal energy is transferred from the treatment region TR, to the needles 228, and then to the cooled medium, thereby preventing the thermal energy from reaching the non-treatment region NTR and maintaining it at a cool temperature. The heated medium is then conveyed from the branched return lumens 240, through the common return lumen 236, and through the main return lumen 232. From the main return lumen 232, the heated medium travels through the outlet fluid port 224 on the handle 218, through the tubing 199, and into the discharge reservoir 186.

Figure 12A:
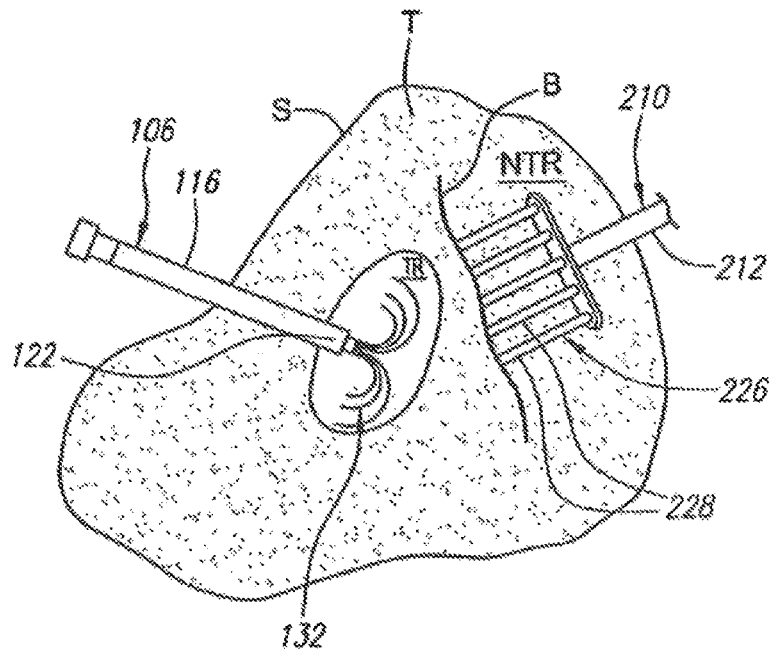
FIGS. 12A-12B illustrate cross-sectional views of another preferred method of using the tissue treatment system of FIG. 1 to treat target tissue, wherein the cooling probe of FIG. 8 is used to thermally protect adjacent tissue.
Figure 12B:
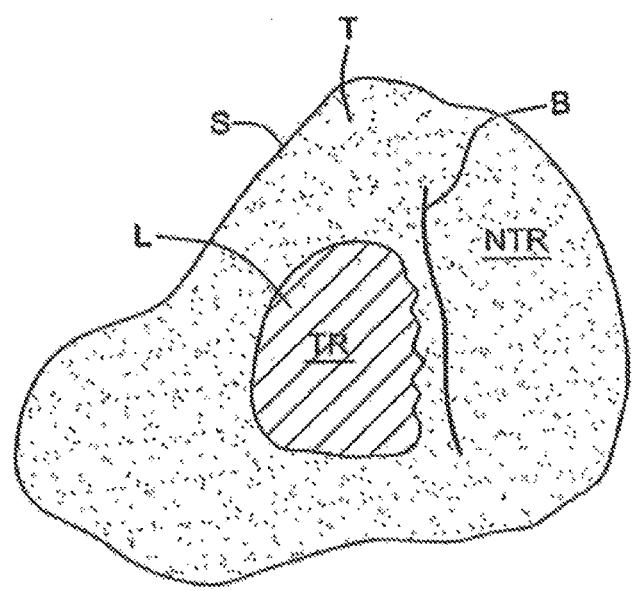

The RF generator 108 is then operated to ablate the treatment region TR. Specifically, a lesion L is formed within the treatment region TR, as illustrated in FIG. 12B. Because the actively cooled needle array 226 forms a thermal barrier between the treatment region TR and the non-treatment region NTR, the lesion L does not extend to the non-treatment NTR, but instead exhibits a scalloped contour that extends along the barrier B.

Figure 13:
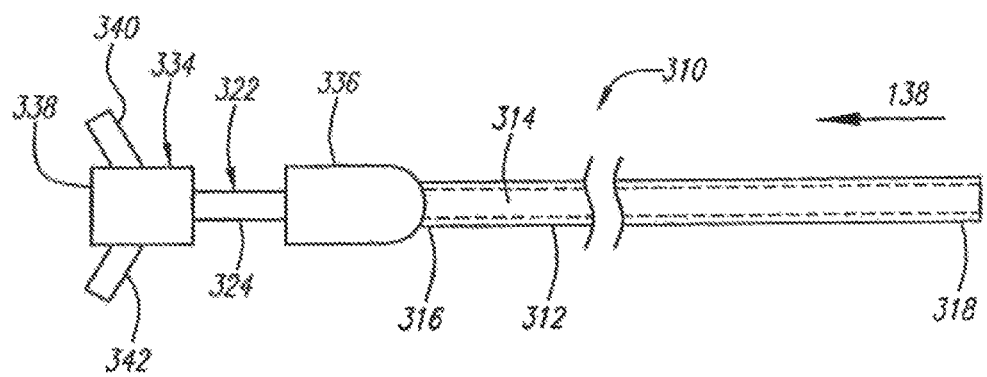
FIG. 13 is a side view of another cooling probe that can be used in the tissue treatment system of FIG. 1, particularly showing the needle array retracted.
Figure 14:
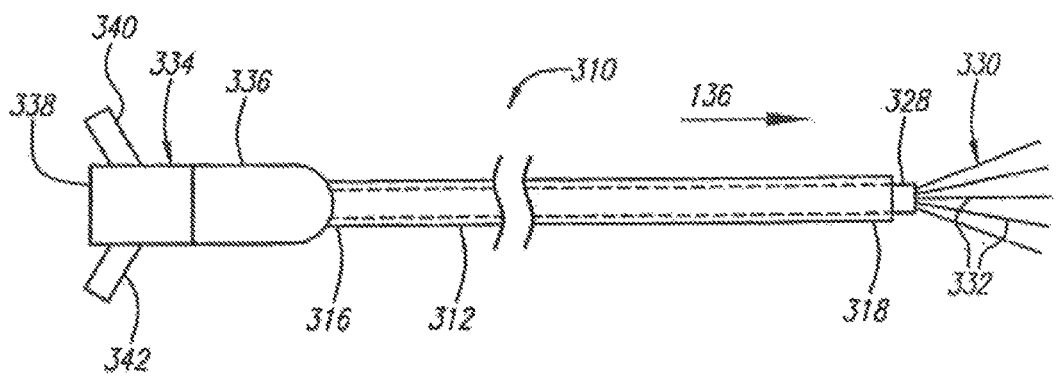
FIG. 14 is a side view of the cooling probe of FIG. 13 that can be used in the tissue treatment system of FIG. 1, particularly showing the needle array deployed into a fan-shaped configuration.

Referring to FIGS. 13 and 14, a cooling probe 310 that can be used in the cooling subsystem 104 is illustrated. The cooling probe 310 is generally similar in structure to the ablation probe assembly 106 in that it comprises an elongate cannula 312 and an inner probe 314 slidably disposed within the cannula 312. The cannula 312 has a proximal end 316, a distal end 318, and a central lumen 320 (shown in phantom) extending between the proximal and distal ends 316 and 318. The cannula 312 can have a dimension and composition similar to that described above with respect to the cannula 116 of the ablation probe assembly 106. The inner probe 314 comprises a reciprocating shaft 322 (shown best in FIG. 15) having a proximal end 324 and a distal end 326, a cooling manifold 328 mounted to the distal end 326 of the shaft 322, and an array 330 of tissue penetrating cooling needles 332 extending from the manifold 328. Like the cannula 312, the shaft 322 is composed of a suitable material, such as plastic, metal or the like. Like the shaft 322 of the ablation probe assembly 106, it can be appreciated that longitudinal translation of the shaft 322 relative to the cannula 312 in the distal direction 136 deploys the cooling needle array 330 from the distal end 318 of the cannula 312

(FIG. 14), and longitudinal translation of the shaft 322 relative to the cannula 312 in the proximal direction 138 retracts the cooling needle array 330 into the distal end 318 of the cannula 312 (FIG. 13).

The cooling needles 332 are of similar construction and composition as the previously described needle electrodes 134. That is, each cooling needle 332 is preferably composed of a single wire that is formed from resilient conductive metals having a suitable shape memory, such as stainless steel, nickel-titanium alloys, nickel-chromium alloys, spring steel alloys, and the like. The wires may have circular or non-circular cross-sections. The distal ends of the cooling needles 332 may be honed or sharpened to facilitate their ability to penetrate tissue. The distal ends of these cooling needles 332 may be hardened using conventional heat treatment or other metallurgical processes. The diameter and length of the needles 332 are preferably within the range of 0.5 mm to 4.0 mm, and 5 cm to 25 cm, respectively.

When deployed from the cannula 312 (FIG. 14), the needle array 330 is placed in a fan-shaped configuration. As with the previously described needle array 226, the needles 332 are arranged in a series to maximize the cooling efficiency of cooling probe 310. In the illustrated embodiment, the needle array 330 is arranged in a rectilinear pattern, but can also be arranged in a curvilinear pattern or can be staggered.

The cooling probe 310 further comprises a handle assembly 334, which includes a connector sleeve 336 mounted to the proximal end 316 of the cannula 312 and a connector member 338 slidably engaged with the sleeve 310 and mounted to the proximal end 324 of the shaft 322. The connector member 338 of the handle assembly 334 comprises an inlet fluid port 340 and an outlet fluid port 342. The handle assembly 334 can be composed of any suitable rigid material, such as, e.g., metal, plastic, or the like.

Figure 15:
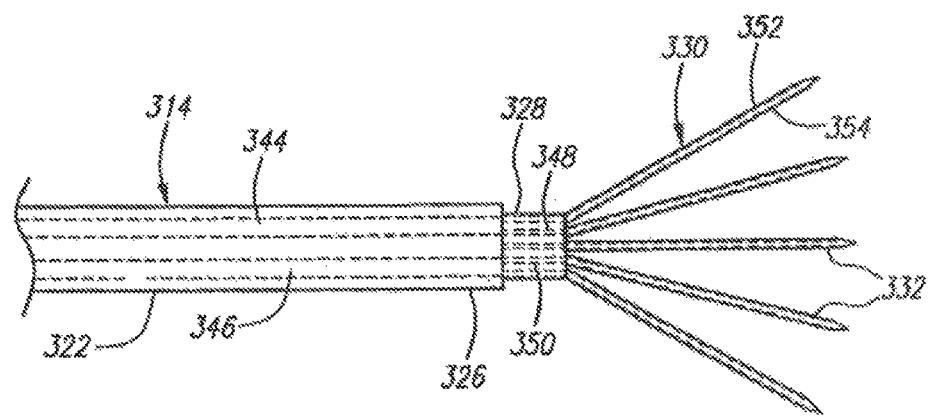
FIG. 15 is a partially cutaway view of an inner probe used in the cooling probe of FIG. 13.

Referring now to FIG. 15, the cooling probe 310 further comprises a coolant flow conduit (shown in phantom) that serves to cool the needles 332, and thus the tissue in contact with the needle array 330, by thermally drawing heat away. In particular, the coolant flow conduit comprises a main cooling lumen 344 that is in fluid communication with the inlet fluid port 340 of the handle assembly 334 and extends through the shaft 322, a network of cooling lumens 348 in fluid communication with the main cooling lumen 344 and extending through the cooling manifold 328, and a plurality of cooling lumens 352 that are in fluid communication with the network of cooling lumens 348 and extend through the needles 332. The coolant flow conduit also comprises a main return lumen 346 that is in fluid communication with the outlet fluid port 342 of the handle assembly 334 and extends through the shaft 322, a network of return lumens 348 in fluid communication with the main return lumen 346 and extending through the cooling manifold 328, and a plurality of return lumens 354 that are in fluid communication with the network of return lumens 348 and extend through the needles 332. The distal ends of the cooling lumens 352 are in fluid communication with the respective distal ends of the return lumens 354 to complete the cooling circuit.

Figure 16A:
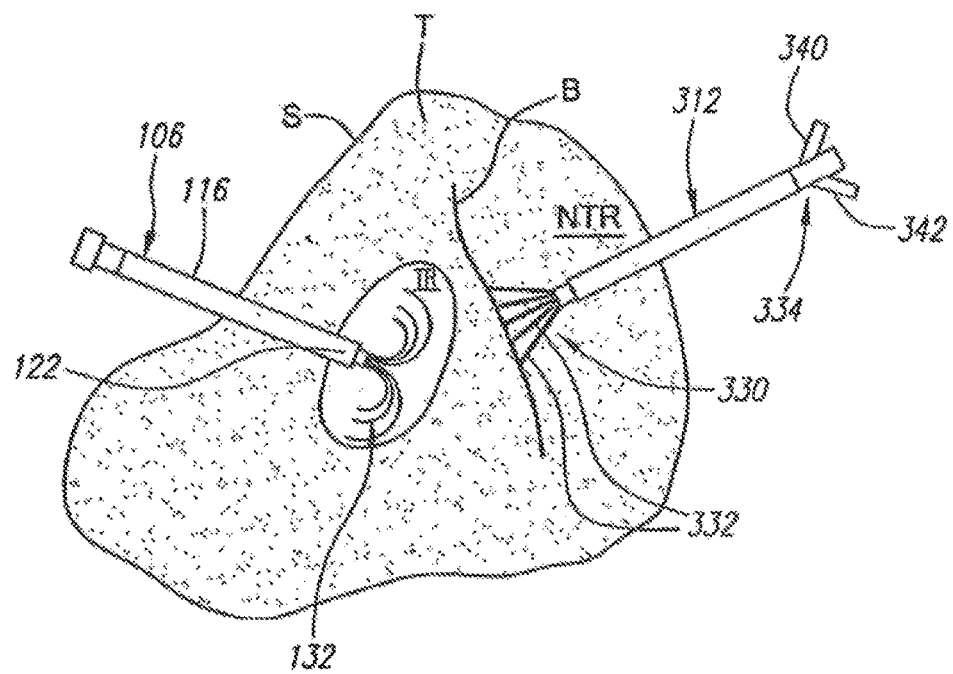
FIGS. 16A-16B illustrate cross-sectional views of still another preferred method of using the tissue treatment system of FIG. 1 to treat target tissue, wherein the cooling probe of FIG. 13 is used to thermally protect adjacent tissue.

Operation of the cooling probe 310 is similar to the operation of the cooling probe 210, with the exception that the array of needles 332 can be deployed during a percutaneous or laparoscopic procedure. Specifically, the electrode array 132 of the ablation probe assembly 106 is deployed within the target tissue TR, as illustrated in FIG. 7. The needle array 330 of the cooling probe 312 is deployed from the distal end 318 of the cannula 312 into the tissue, so that the needles 332 lie along a boundary B separating the treatment region TR from the non-treatment region NTR, as illustrated in FIG. 16A. The pump assembly 114 is then operated to convey the cooling medium through the needles 332, thereby providing a thermal barrier between the treatment region TR and the non-treatment region NTR. Specifically, the power head 180 conveys the cooled medium from the syringe 182 under positive pressure, through the tubing 198, and into the inlet fluid port 340 on the handle 334. The cooled medium then travels through the main cooling lumen 344, through the network of cooling lumens 348 within the manifold 328, and into the cooling lumens 352 within the needles 332. Thermal energy is transferred from the treatment region TR, to the needles 332, and then to the cooled medium, thereby preventing the thermal energy from reaching the non-treatment region NTR and maintaining it at a cool temperature. The heated medium is then conveyed from the return lumens 354, through the network of return lumens 350 within the manifold 328, and into the main return lumen 346. From the main return lumen 346, the heated medium travels through the outlet fluid port 342 on the handle 334, through the tubing 199, and into the discharge reservoir 186.

Figure 16B:
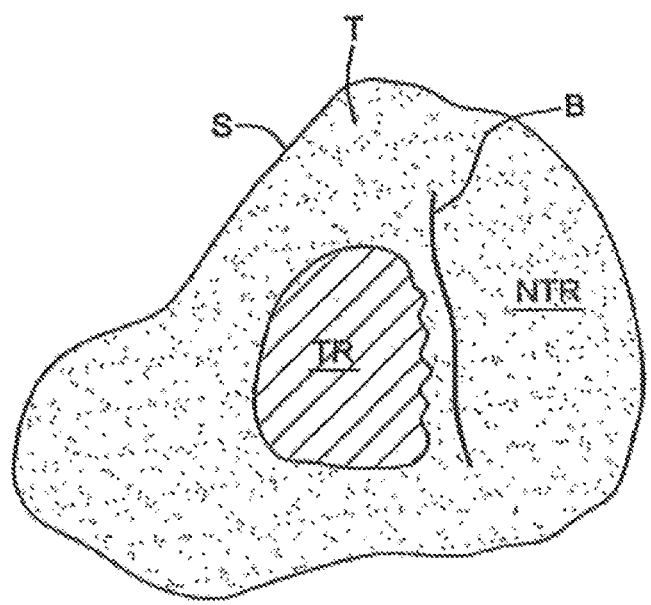

The RF generator 108 is then operated to ablate the treatment region TR. Specifically, a lesion L is formed within the treatment region TR, as illustrated in FIG. 16B. Because the actively cooled needle array 330 forms a thermal barrier between the treatment region TR and the non-treatment region NTR, the lesion L does not extend to the non-treatment NTR, but instead exhibits a scalloped contour that extends along the barrier 8.

Figure 17:
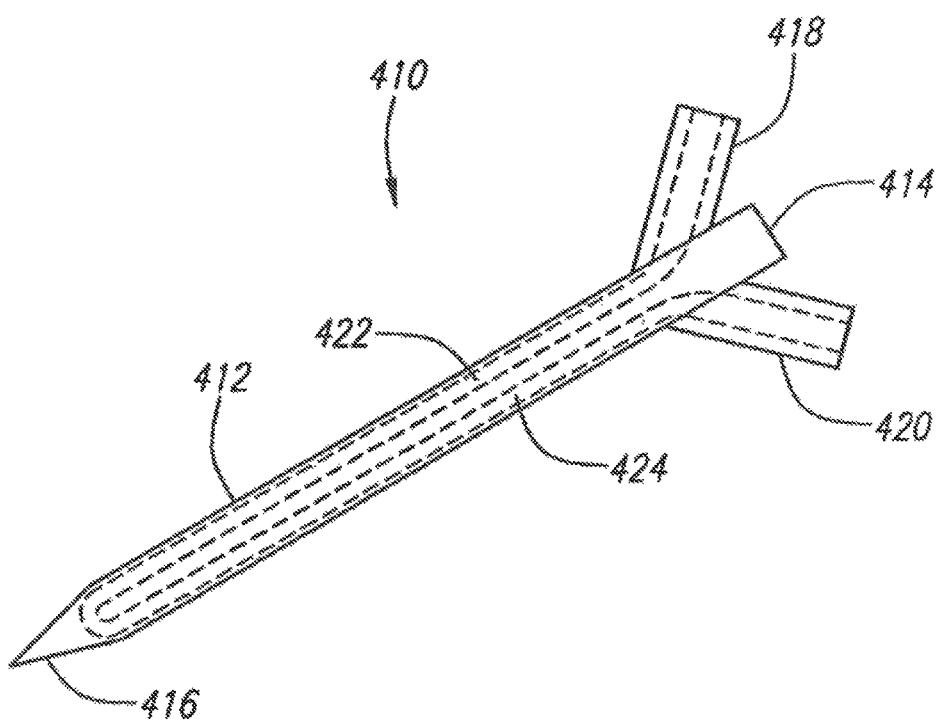
FIG. 17 is a side view of another cooling probe that can be used in the tissue treatment system of FIG. 1.

Referring to FIG. 17, a single cooling needle 410 that can be used in the cooling subsystem 104 is illustrated. The needle 410 comprises a shaft 412, a proximal end 414, and a distal end 416, and is composed of a rigid thermally conductive material, such as, e.g., stainless steel. The needle 410 can have any cross-section as long as it is capable of penetrating tissue, but in the preferred embodiment, its cross-section is circular, oval or flat. The diameter and length of the needle 410 is preferably within the range of 0.5 mm to 4.0 mm, and 5 cm to 25 cm, respectively. The needle 410 comprises an inlet fluid port 418 and an outlet fluid port 420 formed at its proximal end 414 for connection to the pump assembly 114. The needle 410 further comprises a coolant flow conduit (shown in phantom) that serves to cool the shaft 412, and thus the tissue in contact with the shaft 412, by thermally drawing heat away. In particular, the coolant flow conduit comprises a cooling lumen 422 that is in fluid communication with the inlet fluid port 418 and extends through the shaft 412, and a return lumen 424 that is in fluid communication with the outlet fluid port 420 and extends through the shaft 412. The distal end of the cooling lumen 422 is in fluid communication with the distal end of the return lumen 424 to complete the cooling circuit.

Figure 18A:
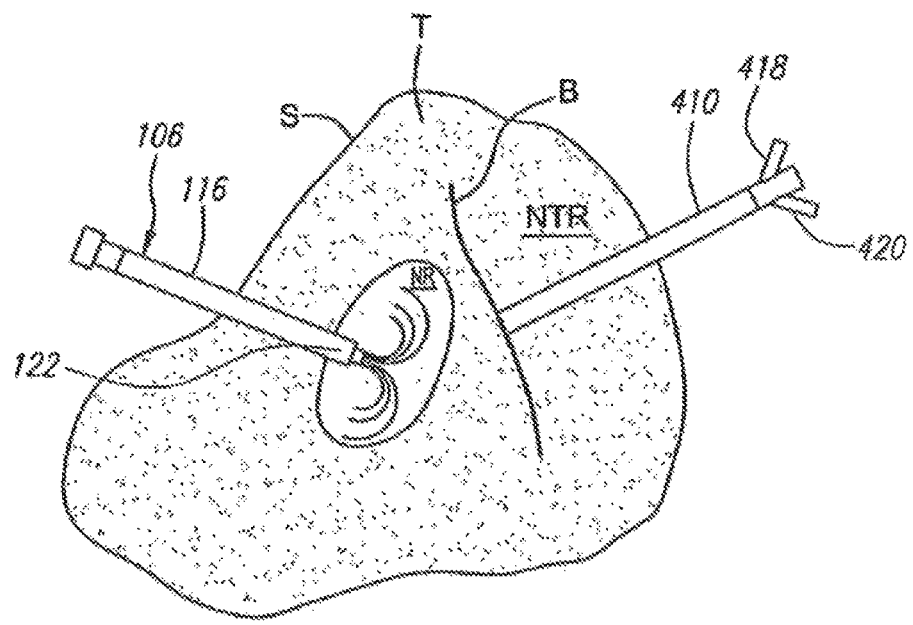
FIGS. 18A-18B illustrate cross-sectional views of yet another preferred method of using the tissue treatment system of FIG. 1 to treat target tissue, wherein the cooling probe of FIG. 17 is used to thermally protect adjacent tissue.

Operation of the cooling needle 410 is similar to the operation of the cooling probe 310, with the exception that the cooling needle 410 is percutaneously introduced through the skin of the patient or through a surgical opening into the tissue. Specifically, the electrode array 132 of the ablation probe assembly 106 is deployed within the target tissue TR. The cooling needle 410 is inserted, percutaneously or through a surgical opening, into the tissue T on the boundary B separating the treatment region TR from the non-treatment region NTR, as illustrated in FIG. 18A. The pump assembly 114 is then operated to convey the cooling medium through the needle 410, thereby providing a thermal barrier between the treatment region TR and the non-treatment region NTR. Specifically, the power head 180 conveys the cooled medium from the syringe 182 under positive pressure, through tubing 198, and into the inlet fluid port 418. The cooled medium then travels through the cooling lumen 422 of the needle 412. Thermal energy is transferred from the treatment region TR, to the shaft 412 of the needle 410, and then to the cooled medium, thereby preventing the thermal energy from reaching the non-treatment region NTR and maintaining it at a cool temperature. The heated medium is then conveyed from the return lumen 424, through the outlet fluid port 420, through the tubing 199, and into the discharge reservoir 186.

Figure 18B:
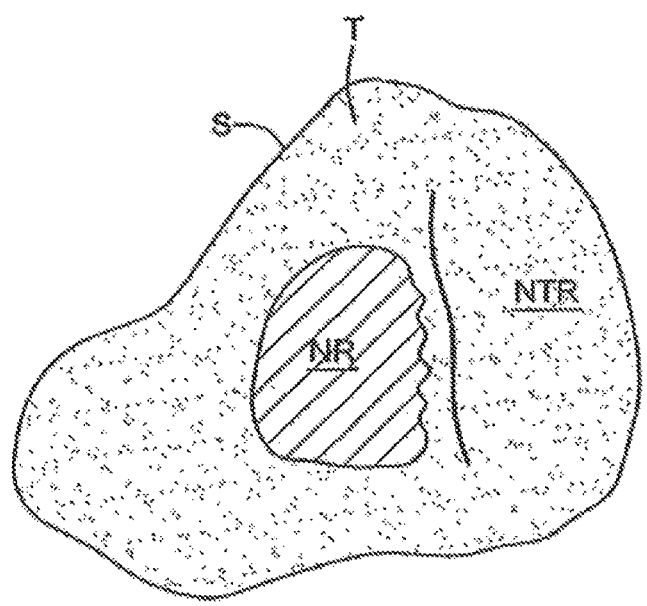

The RF generator 108 is then operated to ablate the treatment region TR. Specifically, a lesion L is formed within the treatment region TR, as illustrated in FIG. 18B. Because the actively cooled needle 410 forms a thermal barrier between the treatment region TR and the non-treatment region NTR, the lesion L does not extend to the non-treatment NTR In alternative methods, multiple needles 410 can be inserted along the length of the boundary B to provide a broader thermal barrier, in which case a scalloped lesion L will be formed similar to those illustrated in FIGS. 12B and 16B. The tubings 198 and 199 of the pump assembly 114 can be branched in order to feed the medium to, and remove the heated medium from, the multiple needles 410.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical system, comprising:
    a barrier probe comprising:
        an elongate shaft having a distal end and a proximal end; and
        a barrier element at the distal end of the barrier probe, the barrier element having an unexpanded delivery state and an expanded barrier state with a surface area configured to separate tissue targeted for treatment and one or more adjacent regions to be protected; and
    a treatment probe comprising:
        an elongate member having a proximal end and a distal end; and
        a needle element at the distal end of the elongate member.

2. The medical system of claim 1, wherein the barrier element is a balloon.

3. The medical system of claim 2, wherein the barrier probe includes a supply lumen and a return lumen in fluid communication with the balloon.

4. The medical system of claim 1, wherein the needle element comprises an array of needles.

5. The medical system of claim 1, wherein the tissue targeted for treatment is diseased tissue and the one or more adjacent regions to be protected is healthy tissue.

6. The medical system of claim 1, wherein the needle element is conductive and configured to deliver ablative RF energy.

7. The medical system of claim 1, wherein the barrier element is a thermal barrier.

8. The medical system of claim 1, wherein the barrier element includes a contained interior that is cooled by a medium circulated through the barrier element.

9. The medical system of claim 1, wherein the barrier element is concave and configured to conform to a curved surface of an organ.

10. The medical system of claim 1, wherein the barrier is compliant and conforms in use to the tissue targeted for treatment and the one or more adjacent regions to be protected.

11. A method of separating tissue targeted for treatment and one or more adjacent regions to be protected, comprising:
    introducing an elongate barrier probe with a barrier balloon in an unexpanded delivery state to a position separating the target tissue from the one or more adjacent regions to be protected, wherein the barrier balloon is mounted to a distal end of the elongate barrier probe;
    expanding the barrier balloon to conform to the one or more adjacent regions to be protected;
    inserting a treatment probe into the target tissue; and
    treating the target tissue while protecting the one or more adjacent regions separated by the barrier.

12. The method of claim 11, wherein the barrier probe includes a supply lumen and a return lumen in fluid communication with the balloon.

13. The method of claim 11, wherein the target tissue is diseased tissue and the one or more adjacent regions to be protected is healthy tissue.

14. The method of claim 13, wherein the energy is ablative RF energy.

15. The method of claim 11, wherein the barrier balloon is a thermal barrier.

16. The method of claim 15, wherein the barrier balloon is cooled by a medium circulated through the barrier balloon.

17. The method of claim 11, wherein the barrier balloon is compliant and conforms in use on opposed sides of the barrier balloon to the tissue targeted for treatment and the one or more adjacent regions to be protected.

\* \* \* \* \*